US011512319B2

(12) United States Patent
Lu et al.

(10) Patent No.: US 11,512,319 B2
(45) Date of Patent: Nov. 29, 2022

(54) TRANSCRIPTION FACTOR SUGR CODING GENE, AND USE THEREOF IN PRODUCTION OF N-ACETYLGLUCOSAMINE

(71) Applicants: JIANGNAN UNIVERSITY, Wuxi (CN); SHANDONG RUNDE BIOTECHNOLOGY CO., LTD., Taian (CN)

(72) Inventors: Jianxing Lu, Taian (CN); Long Liu, Wuxi (CN); Jian Chen, Wuxi (CN); Changfeng Liu, Taian (CN); Xueqin Lv, Wuxi (CN); Guocheng Du, Wuxi (CN); Jianghua Li, Wuxi (CN); Chen Deng, Taian (CN); Jiangong Lu, Taian (CN)

(73) Assignees: JIANGNAN UNIVERSITY, Jiangsu (CN); SHANDONG RUNDE BIOTECHNOLOGY CO., LTD., Shandong (CN)

( * ) Notice: Subject to any disclaimer, the term of this patent is extended or adjusted under 35 U.S.C. 154(b) by 0 days.

(21) Appl. No.: 17/264,775

(22) PCT Filed: Jan. 7, 2020

(86) PCT No.: PCT/CN2020/070593
§ 371 (c)(1),
(2) Date: Jan. 29, 2021

(87) PCT Pub. No.: WO2021/128464
PCT Pub. Date: Jul. 1, 2021

(65) Prior Publication Data
US 2022/0090101 A1 Mar. 24, 2022

(30) Foreign Application Priority Data
Dec. 25, 2019 (CN) .......................... 201911358364.6

(51) Int. Cl.
*C12N 15/77* (2006.01)
*C12N 1/20* (2006.01)
*C07K 14/34* (2006.01)
*C12P 19/26* (2006.01)

(52) U.S. Cl.
CPC .............. *C12N 15/77* (2013.01); *C07K 14/34* (2013.01); *C12N 1/205* (2021.05); *C12P 19/26* (2013.01)

(58) Field of Classification Search
CPC ........ C12N 15/77; C12N 1/205; C07K 14/34; C12P 19/26
See application file for complete search history.

(56) References Cited

FOREIGN PATENT DOCUMENTS

| CN | 108424870 A | 8/2018 |
|---|---|---|
| CN | 110195036 A | 9/2019 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Engels et al., Journal of Bacteriology 189(8):2955-2966, 2007.*
Deng et al., "Metabolic engineering of Corynebacterium glutamicum S9114 based on whole-genome sequencing for e!cient N-acetylglucosamine synthesis" Synthetic and Systems Biotechnology 4 (2019) 120-129 (Jun. 6, 2019).
Niu et al, "Research progress on microbiologyical synthesis of N-acetylglucosamine and its derivatives" Food and Fermentation Industries, 2020, 46(1): 274-279 (Oct. 16, 2019).

* cited by examiner

*Primary Examiner* — Delia M Ramirez
(74) *Attorney, Agent, or Firm* — SZDC Law P.C.

(57) ABSTRACT

The present invention provides a recombinant *Corynebacterium glutamicum* producing N-acetylglucosamine and use thereof. The recombinant *Corynebacterium glutamicum* is obtained by overexpressing, in *Corynebacterium glutamicum*, the transcription factor SugR derived therefrom. The recombinant *Corynebacterium glutamicum* of the present invention increases the production of acetylglucosamine to up to 26 g/L, and lays a foundation for further metabolic engineering of *Corynebacterium glutamicum* to produce glucosamine.

5 Claims, 3 Drawing Sheets
Specification includes a Sequence Listing.

SEQUENCE LISTING

```
<160> NUMBER OF SEQ ID NOS: 13

<210> SEQ ID NO 1
<211> LENGTH: 945
<212> TYPE: DNA
<213> ORGANISM: Artificial sequence
<220> FEATURE:
<223> OTHER INFORMATION: L-lactate dehydrogenase coding gene

<400> SEQUENCE: 1
```

```
atgaaagaaa ccgtcggtaa caagattgtc ctcattggcg caggagatgt tggagttgca    60
tacgcatacg cactgatcaa ccagggcatg cagatcacc ttgcgatcat cgacatcgat    120
gaaaagaaac tcgaaggcaa cgtcatggac ttaaaccatg gtgttgtgtg ggccgattcc    180
cgcacccgcg tcaccaaggg cacctacgct gactgcaag acgcagccat ggttgtcatt    240
tgtgccggcg cagcccaaaa gccaggcgag acccgcctcc agctggtgga caaaaacgtc    300
aagattatga atccatcgt cggcgatgtc atggacagcg gattcgacgg catcttcctc    360
gtggcgtcca acccagtgga tatcctgacc tacgcagtgt ggaaattctc cggcttggaa    420
tggaaccgcg tgatcggctc cggaactgtc ctggactccg ctcgattccg ctacatgctg    480
ggcgaactct acgaagtggc accaagctcc gtccacgcct acatcatcgg cgaacacggc    540
gacactgaac ttccagtcct gtcctccgcg accatcgcag gcgtatcgct tagccgaatg    600
ctggacaaag acccagagct tgagggccgt ctagagaaaa ttttcgaaga cacccgcgac    660
gctgcctatc acattatcga cgccaagggc tccacttcct acggcatcgg catgggtctt    720
gctcgcatca cccgcgcaat cctgcagaac caagacgttg cagtcccagt ctctgcactg    780
ctccacggtg aataccgtga ggaagacatc tacatcggca ccccagctgt ggtgaaccgc    840
cgaggcatcc gccgcgttgt cgaactagaa atcaccgacc acgagatgga acgcttcaag    900
cattccgcaa ataccctgcg cgaaattcag aagcagttct tctaa                   945
```

<210> SEQ ID NO 2
<211> LENGTH: 33
<212> TYPE: DNA
<213> ORGANISM: Artificial sequence
<220> FEATURE:
<223> OTHER INFORMATION: LdhloxPUF

<400> SEQUENCE: 2
atctcgagtt cgccggtgcg tacttttggt ccg                                 33

<210> SEQ ID NO 3
<211> LENGTH: 37
<212> TYPE: DNA
<213> ORGANISM: Artificial sequence
<220> FEATURE:
<223> OTHER INFORMATION: Primer LdhloxPUR

<400> SEQUENCE: 3
atggatcctc acccgcgcaa tcctacaaaa ccaagac                             37

<210> SEQ ID NO 4
<211> LENGTH: 33
<212> TYPE: DNA
<213> ORGANISM: Artificial sequence
<220> FEATURE:
<223> OTHER INFORMATION: Primer LdhloxPDF

<400> SEQUENCE: 4
acctctagat gttgtcggga ggcccacgca aag                                 33

<210> SEQ ID NO 5
<211> LENGTH: 31
<212> TYPE: DNA
<213> ORGANISM: Artificial sequence
<220> FEATURE:
<223> OTHER INFORMATION: Primer LdhloxPDR

<400> SEQUENCE: 5
ccggaattca agcaatgctg tggcgcagct c    31

<210> SEQ ID NO 6
<211> LENGTH: 30
<212> TYPE: DNA
<213> ORGANISM: Artificial sequence
<220> FEATURE:
<223> OTHER INFORMATION: Primer KanloxpldhF

<400> SEQUENCE: 6
acggatccgc gcaattaacc ctcactaaag    30

<210> SEQ ID NO 7
<211> LENGTH: 30
<212> TYPE: DNA
<213> ORGANISM: Artificial sequence
<220> FEATURE:
<223> OTHER INFORMATION: Primer KanloxpldhR

<400> SEQUENCE: 7
acctctagaa atacgactca ctatagggcg    30

<210> SEQ ID NO 8
<211> LENGTH: 780
<212> TYPE: DNA
<213> ORGANISM: Artificial sequence
<220> FEATURE:
<223> OTHER INFORMATION: Transcription factor SugR

<400> SEQUENCE: 8
atgtacgcag aggagcgccg tcgacagatt gcctcattaa cggcagttga gggacgtgta    60
aatgtcacag aattagcgag ccgattcgat gtcactgcag agacgattcg acgagacctt    120
gcggtgctag accgcgaggg aattgttcac cgcgttcacg gtggcgcagt agccacccaa    180
tctttccaaa ccacagagtt gagcttggat actcgtttca ggtctgcatc gtcagcaaag    240
tactccattg ccaaggcagc gatgcagttc ctgcccgctg agcatggcgg actgttcctc    300
gatgcgggaa ctactgttac tgctttggcc gatctcattt ctgagcatcc tagcgccaag    360
aagtggtcga tcgtgaccaa ctgcctcccc atcgcactta atctggccaa cgccgggctt    420
gatgatgtcc agctgcttgg aggaagcgtt cgcgcgatca cccaggctgt tgtgggtgac    480
actgcgcttc gtactctcgc gctgatgcgt gcggatgtag tgttcatcgg caccaacgcg    540
ttgacgttgg atcacggatt gtctacggcc gattcccaag aggctgctat gaaatctgcg    600
atgatcacca cgcccacaa ggtggtggtg ttgtgtgact ccaccaagat gggcaccgac    660
tacctcgtga gctttggcgc aatcagcgat atcgatgtgg tggtcaccga tgcgggtgca    720
ccagcaagtt tcgttgagca gttgcgagaa cgcgatgtag aagttgtgat tgcagaatga    780

<210> SEQ ID NO 9
<211> LENGTH: 259
<212> TYPE: PRT
<213> ORGANISM: Artificial sequence
<220> FEATURE:
<223> OTHER INFORMATION: Transcription factor SugR

<400> SEQUENCE: 9

Met Tyr Ala Glu Glu Arg Arg Arg Gln Ile Ala Ser Leu Thr Ala Val
 1               5                  10                  15

Glu Gly Arg Val Asn Val Thr Glu Leu Ala Ser Arg Phe Asp Val Thr
            20                  25                  30

Ala Glu Thr Ile Arg Arg Asp Leu Ala Val Leu Asp Arg Glu Gly Ile

```
                    35                  40                  45
Val His Arg Val His Gly Gly Ala Val Ala Thr Gln Ser Phe Gln Thr
 50                  55                  60

Thr Glu Leu Ser Leu Asp Thr Arg Phe Arg Ser Ala Ser Ser Ala Lys
 65                  70                  75                  80

Tyr Ser Ile Ala Lys Ala Ala Met Gln Phe Leu Pro Ala Glu His Gly
                 85                  90                  95

Gly Leu Phe Leu Asp Ala Gly Thr Thr Val Thr Ala Leu Ala Asp Leu
            100                 105                 110

Ile Ser Glu His Pro Ser Ala Lys Lys Trp Ser Ile Val Thr Asn Cys
        115                 120                 125

Leu Pro Ile Ala Leu Asn Leu Ala Asn Ala Gly Leu Asp Asp Val Gln
130                 135                 140

Leu Leu Gly Gly Ser Val Arg Ala Ile Thr Gln Ala Val Val Gly Asp
145                 150                 155                 160

Thr Ala Leu Arg Thr Leu Ala Leu Met Arg Ala Asp Val Val Phe Ile
                165                 170                 175

Gly Thr Asn Ala Leu Thr Leu Asp His Gly Leu Ser Thr Ala Asp Ser
            180                 185                 190

Gln Glu Ala Ala Met Lys Ser Ala Met Ile Thr Asn Ala His Lys Val
        195                 200                 205

Val Val Leu Cys Asp Ser Thr Lys Met Gly Thr Asp Tyr Leu Val Ser
    210                 215                 220

Phe Gly Ala Ile Ser Asp Ile Asp Val Val Thr Asp Ala Gly Ala
225                 230                 235                 240

Pro Ala Ser Phe Val Glu Gln Leu Arg Glu Arg Asp Val Glu Val Val
                245                 250                 255

Ile Ala Glu

<210> SEQ ID NO 10
<211> LENGTH: 45
<212> TYPE: DNA
<213> ORGANISM: Artificial sequence
<220> FEATURE:
<223> OTHER INFORMATION: upstream primer FragmentSugR.FOR

<400> SEQUENCE: 10 ccgtcgaataaaagaaattcggacatatttagtaaattggctttt                 45

<210> SEQ ID NO 11
<211> LENGTH: 36
<212> TYPE: DNA
<213> ORGANISM: Artificial sequence
<220> FEATURE:
<223> OTHER INFORMATION: downstream primer FragmentSugR.REV

<400> SEQUENCE: 11 ctttgctagtcggacttgcagtgactgtaagaatca                          36

<210> SEQ ID NO 12
<211> LENGTH: 34
<212> TYPE: DNA
<213> ORGANISM: Artificial sequence
<220> FEATURE:
<223> OTHER INFORMATION: upstream primer VectorSugR.FOR

<400> SEQUENCE: 12 tgcaagtccgactagcaaaggagaagaaaagccg                            34
```

```
<210> SEQ ID NO 13
<211> LENGTH: 36
<212> TYPE: DNA
<213> ORGANISM: Artificial sequence
<220> FEATURE:
<223> OTHER INFORMATION: downstream primer VectorSugR.REV

<400> SEQUENCE: 13 tccgaatttcttttattcgacggtgacagactttgc                                   36
```

TRANSCRIPTION FACTOR SUGR CODING GENE, AND USE THEREOF IN PRODUCTION OF N-ACETYLGLUCOSAMINE

This application is the National Stage Application of PCT/CN2020/070593, filed on Jan. 7, 2020, which claims priority to Chinese Patent Application No. 201911358364.6, filed on Dec. 25, 2019, which is incorporated by reference for all purposes as if fully set forth herein.

FIELD OF THE INVENTION

The present invention relates to the field of metabolic engineering, and more particularly to a transcription factor SugR coding gene and use thereof in the production of N-acetylglucosamine.

DESCRIPTION OF THE RELATED ART

N-acetylglucosamine (GlcNAc) is a derivative of glucosamine. It is reductive and also an important precursor for the synthesis of bifidus factor and hyalurate. N-acetylglucosamine is also referred to as 2-(acetylamino)-2-deoxyglucose or N-acetylaminoglucose, and is a basic unit constituting a variety of polysaccharides, and has important physiological functions in the body. *Corynebacterium glutamicum* is a gram-positive soil bacterium with high GC content from the Actinobacteria. It has been used in the industrial production of amino acids and is designed to produce various compounds, including polymer building blocks and biofuels. Since the initial publication of the genome sequence, the multifunctional metabolic pathway, the genetic component and the regulatory mechanism in *Corynebacterium glutamicum* have received extensive research. In order to improve the production efficiency by biotechnologies, genetic tools and omics-based analysis methods, including transcriptomics, proteomics, metabolomics and rheology, are developed based on the genome sequence information and are widely used to study the metabolic pathways and its post-transcriptional regulation.

The current research on transcription factors in bacteria (including two-component system and sigma factor) reveals the transcriptional regulatory link between the metabolic pathways and the stress response systems, forming a complex transcriptional regulatory network. Therefore, it is very important to develop a new recombinant bacterium and method for increasing the production of N-acetylglucosamine in *Corynebacterium glutamicum*.

SUMMARY OF THE INVENTION

To solve the above technical problems, an object of the present invention is to provide a transcription factor SugR coding gene and use thereof in the production of N-acetylglucosamine. In the present invention, a recombinant *Corynebacterium glutamicum* with improved N-acetylglucosamine production is obtained by overexpressing the transcription factor SugR in *Corynebacterium glutamicum*.

The following technical solution is adopted in the present invention.

The present invention provides a recombinant *Corynebacterium glutamicum* producing N-acetylglucosamine, which is obtained by overexpressing, in the starting bacterium *Corynebacterium glutamicum*, a transcription factor SugR derived therefrom.

In order to redistribute the carbon metabolic flux in *Corynebacterium glutamicum*, SugR, a transcription factor related to the central metabolism of carbon in *Corynebacterium glutamicum* is overexpressed in the present invention, thereby improving the ability of *Corynebacterium glutamicum* to produce N-acetylglucosamine.

Preferably, the acetylglucosamine deacetylase coding gene NagA, the acetylglucosamine deaminase coding gene GamA and the L-lactate dehydrogenase coding gene ldh in the starting bacterium *Corynebacterium glutamicum* are knocked out.

Preferably, the starting bacterium *Corynebacterium glutamicum* is *C. glutamicum* S9114 ΔnagA-ΔgamA-Δldh. *C. glutamicum* S9114 ΔnagA-ΔgamA-Δldh is obtained by knocking out the L-lactate dehydrogenase coding gene ldh in the starting strain *C. glutamicum* S9114 ΔnagA-ΔgamA. The L-lactate dehydrogenase coding gene ldh is as shown by NCBI-Gene ID: 1020853. The construction method of *C. glutamicum* S9114 ΔnagA-ΔgamA is as described in CN 110195036 A. By knocking out the ldh gene encoding the L-lactate dehydrogenase that catalyzes the conversion of pyruvic acid into lactate, the pathway in the host bacterium *Corynebacterium glutamicum* to synthesize the by-product lactate is blocked.

Preferably, the encoding gene of the transcription factor SugR is as shown by NCBI-GeneID: 1019888, the nucleotide sequence of the transcription factor SugR is as shown in SEQ ID NO:8, and the amino acid sequence encoded by the SugR gene is as shown in SEQ ID NO:9.

SugR is a DeoR-type transcriptional regulator, originally identified as a repressor of the gene encoding the PTS component of glucose uptake in *Corynebacterium glutamicum*, which controls the transcription of the gene encoding lactate dehydrogenase and the gene encoding glycolytic enzyme, and allows more carbon metabolic flux to flow to the GlcNAc production pathway, thereby improving the ability of *Corynebacterium glutamicum* to produce GlcNAc.

More preferably, the gene encoding the transcription factor SugR is expressed by the expression vector pJYW-4-ceN-C.glglmS. The specific construction process of the expression vector pJYW-4-ceN-C.glglmS is as described in Chen Deng, XueqinLv, Yanfeng Liu, Long Liu. Metabolic engineering of *Corynebacterium glutamicum* S9114 based on whole-genome sequencing for efficient N-acetylglucosamine synthesis. Synthetic and Systems Biotechnology, 2019. 4: 120-129.

The present invention also provides a method for constructing the recombinant *Corynebacterium glutamicum* producing N-acetylglucosamine, which includes the following steps:

transforming the expression vector pJYW-4-ceN-C.glglmS-SugR into the host bacterium to obtain the recombinant *Corynebacterium glutamicum* producing N-acetylglucosamine.

Preferably, the host bacterium is *Corynebacterium glutamicum* in which the acetylglucosamine deacetylase encoding gene NagA, acetylglucosamine deaminase encoding gene GamA, and L-lactate dehydrogenase encoding gene ldh are knocked out.

Preferably, the host bacterium is *C. glutamicum* S9114 ΔnagA-ΔgamA-Δldh, which is constructed by the following steps:

knocking out the acetylglucosamine deacetylase coding gene NagA, the acetylglucosamine deaminase coding gene GamA and the L-lactate dehydrogenase coding gene ldh in *C. glutamicum* S9114 sequentially by making use of the gene knockout frame of the acetylglucosamine deacetylase coding gene NagA, the gene knockout frame of the acetylglucosamine deaminase coding gene GamA, and the gene knockout frame of the L-lactate dehydrogenase coding gene ldh.

C. glutamicum S9114 ΔnagA-ΔgamA-Δldh is obtained by knocking out the L-lactate dehydrogenase coding gene ldh in the starting strain C. glutamicum S9114 ΔnagA-ΔgamA. The construction method of C. glutamicum S9114 ΔnagA-ΔgamA is as described in CN 110195036 A. On this basis, the gene knockout frame of the L-lactate dehydrogenase coding gene ldh is constructed. After homologous recombination, the L-lactate dehydrogenase coding gene ldh in the genome of C. glutamicum S9114 ΔnagA-ΔgamA is replaced by the kanamycin-resistant gene kana in the gene knockout frame of ldh.

More specifically, the construction method of pJYW-4-ceN-C.glglmS-SugR comprises the following steps:

(1) designing amplification primers according to the genome of S9114 to amplify SugR, where upstream primer FragmentSugR.FOR:

5'--CCGTCGAATAAAAGAAATTCGGACATATTTAGTAAATTGGC

TTTT--3';

downstream primer FragmentSugR.REV:

5'--CTTTGCTAGTCGGACTTGCAGTGACTGTAAGAATCA--3';

and designing primers for linearizion of the vector pJYW-4-ceN-C.glglmS upstream primer VectorSugR.FOR:

5'--TGCAAGTCCGACTAGCAAAGGAGAAGAAAAGCCG--3';

downstream primer VectorSugR.REV:

5'--TCCGAATTTCTTTTATTCGACGGTGACAGACTTTGC--3';

and (2) extracting the linearized vector obtained by PCR and the target gene fragment carrying a homologous end of the vector and ligating by a fast cloning kit at a molar ratio of 3:1 to construct the recombinant expression vector pJYW-4-ceN-C.glglmS-SugR.

Preferably, in Step (2), the rapid cloning kit is the ClonExpress II One Step Cloning Kit from Vazyme Biotech Co., Ltd.

The present invention further discloses use of the recombinant Corynebacterium glutamicum in the production of N-acetylglucosamine.

Preferably, N-acetylglucosamine is produced by fermentation using the shake flask method.

In one embodiment of the present invention, a seed culture of recombinant Corynebacterium glutamicum cultured at 28-30° C. and 220 rpm for 16 h is inoculated into a fermentation medium in an amount to give an initial $OD_{562}$ value of 1.6 of the fermentation medium, and incubated at 28-30° C. and 220 rpm for 72-100 h.

By means of the above solution, the present invention has at least the following advantages.

According to the method for constructing a genetically engineered strain that can increase the production of N-acetylglucosamine, in Corynebacterium glutamicum, acetylglucosamine deacetylase coding gene NagA, acetylglucosamine deaminase coding gene GamA, and L-lactate dehydrogenase coding gene ldh are knocked out, the coding gene of the global carbon metabolism regulator transcription factor SugR of Corynebacterium glutamicum is amplified by PCR and then the gene is ligated to the shuttle expression vector pJYW-4-ceN-C.glglmS of Corynebacterium glutamicum and E. coli, whereby the distribution of intracellular carbon metabolism is impacted, the extracellular accumulation of N-acetylglucosamine is increased, with a maximum concentration up to 26 g/L, and a foundation is laid for further metabolic engineering of Corynebacterium glutamicum to produce glucosamine. The method for constructing recombinant Corynebacterium glutamicum in the invention is simple, and convenient in use, thus having good application prospects.

The above description is only a summary of the technical solutions of the present invention. To make the technical means of the present invention clearer and implementable in accordance with the disclosure of the specification, the preferred embodiments of the present invention will be described in detail with reference to the accompanying drawings.

DETAILED DESCRIPTION OF THE PREFERRED EMBODIMENTS

The specific embodiments of the present invention will be described in further detail with reference to embodiments. The embodiments are intended to illustrate the present invention, instead of limiting the scope of the present invention.

(1) In the following examples of the present invention, the determination method of N-acetylglucosamine is as follows:

High performance liquid chromatography (HPLC): Agilent 1260, RID detector, HPX-87H column (Bio-Rad Hercules, Calif.), mobile phase: 5 mM $H_2SO_4$, flow rate 0.6 mL/min, column temperature 35° C., injection volume 10 μL.

(2) In the following examples of the present invention, the culture media used are as follows:

Liquid seed activation medium (LBG)(g/L): peptone 10.0, yeast extract 5.0, NaCl 10.0, glucose 5.0, where the filling volume is 20 ml per 250 ml Erlenmeyer flask.

Solid seed activation medium (LBG solid) (g/L): peptone 10.0, yeast powder 5.0, NaCl 10.0, glucose 5.0, nutrient agar 15.0-20.0.

Competent medium (g/L): peptone 10.0, yeast extract 5.0, NaCl 10.0, glycine 30.0, isoniazid 4.0, and 10 ml of Tween 80, where the filling volume is 50 ml per 500 ml Erlenmeyer flask.

Recovery medium after electroporation LBHIS (g/L): peptone 5.0, yeast extract 2.5, NaCl 5.0, brain heart infusion 18.5, sorbitol 91.0.

Solid medium for transformant detection (g/L): peptone 5.0, yeast extract 2.5, NaCl 5.0, brain heart infusion 18.5, sorbitol 91.0, nutrient agar 15.0-20.0.

Seed culture medium (g/L): glucose 25.0, corn steep liquor 20.0, $KH_2PO_4$ 1.0, $(NH_4)_2SO_4$ 0.5, urea 1.25, pH 7.0.

Fermentation medium (g/L): glucose 40.0, corn steep liquor 20.0, $KH_2PO_4$ 1.0, $(NH_4)_2SO_4$ 20.0, $MgSO_4$ 0.5, $CaCO_3$ 20.0, pH 7.0.

Optimized fermentation medium (g/L): glucose 100.0, corn steep liquor 10.0, $KH_2PO_4$ 1.0, $(NH_4)_2SO_4$ 20.0, $MgSO_4$ 0.5, $CaCO_3$ 20.0, $FeSO_4$ 0.18, pH 7.0.

Sterilization conditions: 115° C., 20 min. 25 mg/L Kanamycin sulfate is added to all media for transformant detection or recombinant culture.

Example 1: Knockout of L-Lactate Dehydrogenase Coding Gene (Ldh)

According to the upstream and downstream sequences of L-lactate dehydrogenase coding gene (ldh) (having a nucleotide sequence as shown in SEQ ID NO:1) in *Corynebacterium glutamicum* ATCC 13032 published on NCBI, amplification primers for knocking out the homologous arms were designed. The upstream and downstream primers for the left arm were respectively LdhloxPUF (having a nucleotide sequence as shown in SEQ ID NO:2) and LdhloxPUR (having a nucleotide sequence as shown in SEQ ID NO:3). The upstream and downstream primers for the right arm were respectively LdhloxPDF (having a nucleotide sequence as shown in SEQ ID NO:4) and LdhloxPDR (having a nucleotide sequence as shown in SEQ ID NO:5). By using the genome DNA of *Corynebacterium glutamicum* strain 59114 as a template, the left and right arms were respectively amplified by PCR.

The primers KanloxpldhF (having a nucleotide sequence as shown in SEQ ID NO:6) and KanloxpldhR (having a nucleotide sequence as shown in SEQ ID NO:7) were designed according to the nucleotide sequence of loxp-kana-loxp gene on the plasmid pDTW-202 (provided by Dr. Wang Xiaoyuan of Jiangnan University), and by using the plasmid pDTW-202 as a template, the loxp gene and kanamycin resistance gene were amplified for loxp-kana-loxp gene. By restriction enzyme cleavage and ligation, the left arm after enzymatic cleavage with the fast cleavage enzyme XhoI/XbaI for 2 hours, the loxp-kana-loxp gene fragment after enzymatic cleavage with the fast cleavage enzyme XbaI/BamHI for 2 hours, the right arm after enzymatic cleavage with the fast cleavage enzyme BamHI/EcoRI for 2 hours, and the plasmid pBluescriptIISK (+) after enzymatic cleavage with the fast cleavage enzyme XhoI/EcoRI for 2 hours (provided by Dr. Xiaoyuan Wang of Jiangnan University) were ligated overnight with T4 ligase at 16° C.

The constructed pBluescriptIISK (+) ligated system with the ldh knockout frame was transformed into *E. coli* JM109 competent cells (see the instruction of Takara Preparation Kit for Competent *Escherichia coli* for the preparation method; article number: 9128). The transformant that was confirmed to be correct by colony PCR was sequenced for verification, to obtain the recombinant plasmid pBluescriptIISK (+)-ldh. The recombinant plasmid pBluescriptIISK (+)-ldh was extracted and electroporated into *Corynebacterium glutamicum* S9114-ΔNagA-GamA. The cells were screened in a plate for kanamycin resistance, and verified by colony PCR. It was confirmed that both the left and right arms of the knockout frame were bound to the 59114 genome, and the L-lactate dehydrogenase coding gene ldh was knocked out to obtain *Corynebacterium glutamicum* S9114-ΔNagA-GamA-Δldh. After 72 h, the GlcNAc production of this strain was 24.7 g/L.

Example 2: Construction of Recombinant Plasmid pJYW-4-ceN-C.glglmS-SugR and Construction of Recombinant *Corynebacterium glutamicum*

(1) Amplification Primers were Designed According to the Genome of S9114 to Amplify SugR.

Upstream primer FragmentSugR.FOR:

5'--CCGTCGAATAAAAGAAATTCGGACATATTTAGTAAATTGGC TTTT--3'

Downstream primer FragmentSugR.REV:

5'--CTTTGCTAGTCGGACTTGCAGTGACTGTAAGAATCA--3'

Primers for linearizion of the vector pJYW-4-ceN-C.glglmS was also designed. Upstream primer VectorSugR.FOR:

5'--TGCAAGTCCGACTAGCAAAGGAGAAGAAAAGCCG--3'

Downstream primer VectorSugR.REV:

5'--TCCGAATTTCTTTTATTCGACGGTGACAGACTTTGC--3'

Primers FragmentSugR.FOR and FragmentSugR.REV were used, and the laboratory-preserved *Corynebacterium glutamicum* S9114 was used as a template. PCR conditions: pre-denaturation at 95° C. for 10 min; 30 cycles of denaturation at 98° C. for 1 min, annealing at 55° C. for 1 min, and extension at 72° C. for 1 min; and final extension at 72° C. for 10 min. The PCR product was recovered with a DNA purification kit. The SugR gene was amplified from the genome of *Corynebacterium glutamicum* S9114, and the SugR gene was amplified by LA Taq HS DNA polymerase.

The plasmid pJYW-4-ceN-C.glglmS previously constructed in the laboratory was used as an expression vector to express the SugR gene, and the specific construction process of pJYW-4-ceN-C.glglmS plasmid was as described in Chen Deng, XueqinLv, Yanfeng Liu, Long Liu. Metabolic engineering of *Corynebacterium glutamicum* S9114 based on whole-genome sequencing for efficient N-acetylglucosamine synthesis. Synthetic and Systems Biotechnology, 2019. 4: 120-129.

Primers VectorSugR.FOR and VectorSugR.REV were used, and the extracted plasmid pJYW-4-ceN-C.glglmS was used as a template. PCR conditions: pre-denaturation at 95° C. for 3 min; 30 cycles of denaturation at 98° C. for 1 min, annealing at 55° C. for 1 min, and extension at 72° C. for 1 min; and final extension at 72° C. for 10 min. The PCR product was recovered with a DNA purification kit to obtain the linearized plasmid pJYW-4-ceN-C.glglmS.

(2) The ClonExpress II One Step Cloning Kit from Vazyme Biotech Co., Ltd. Was used for ligation. The linearized vector obtained by PCR and the target gene fragment carrying a homologous end of the vector were mixed at a molar ratio of 3:1 after extraction, 4 μL of 5×CE II Buffer and 2 μL of Exnase II were added, and then ddH$_2$O was added to give a total volume of the ligation system of 20 μL. The system was reacted at 37° C. for 30 min, and allowed to stand at 4° C. after cooling. Then 10 μL of the ligation system was taken to transform *E. coli*.BL21(DE3) competent cells (see the instruction of Takara Preparation Kit for Competent *Escherichia coli*). The transformant that was confirmed to be correct by colony PCR was selected, sent to GENEWIZ, Inc. and sequenced for verification, to obtain the recombinant expression vector pJYW-4-ceN-C.glglmS-SugR. The vector pJYW-4-ceN-C.glglmS-SugR was deposited at the China Center for Type Culture Collection, Wuhan University, Wuhan, China 430072, on Aug. 4, 2022, with CCTCC No. M20221239.

The plasmid pJYW-4-ceN-C.glglmS-SugR was transformed into *Corynebacterium glutamicum* strain S9114ΔnagA-ΔgamA-Δldh by electroporation.

Preparation of Electrocompetent *Corynebacterium glutamicum*:

(1) *C. glutamicum* was inoculated onto LBG medium (where the cells needed to be picked up from a fresh slant culture, otherwise the growth of the bacteria would be affected), placed on a traveling shaker (200 rpm), and incubated at 30° C. for 16 h until $OD_{562}$ reached 3.0.

(2) 10% was inoculated into a competent medium to allow for an $OD_{562}$ of 0.3, placed on a traveling shaker (200 rpm), and incubated at 30° C. until $OD_{562}$ reached 0.9 (where the incubation time was about 3-5 h, and the cells were in a logarithmic growth phase at this time; and the subsequent operations could also be performed if the $OD_{562}$ was persistently to be low and at about 0.6). The concentration of the cells needed to be ensured to be as high as possible, and the concentration factor was generally 100 times (where 50 mL competent medium was concentrated to 0.5 mL to prepare 5 tubes of competent cells).

(3) The cell suspension was allowed to stand in an ice water bath for 15 min and then centrifuged at 4,000 rpm and 4° C. for 10 min, and the supernatant was discarded carefully.

(4) The cells were fully suspended in 30 mL of pre-cooled 10% glycerol and then centrifuged at 4,000 rpm and 4° C. for 10 min, and the supernatant was discarded carefully. The cells were repeatedly washed 4 times.

(5) The cells (100 times concentrated) were re-suspended in 500 μL of pre-cooled 10% glycerol, and filled in 1.5 mL sterile centrifuge tubes in an amount of 100 μL per tube.

(6) The cells were stored at −80° C. for later use. To ensure the transformation efficiency of competent cells, the cells are preferred to be used immediately after preparation. The cells should not be left for more than 1 week, otherwise the cell content will be released due to the lysis of competent cells, which causes the breakdown of electroporation cuvette during the subsequent electroporation and affects the transformation efficiency.

Electroporation of *Corynebacterium glutamicum*

(1) Competent *Corynebacterium glutamicum* stored at −80° C. were thawed in an ice bath.

(2) 1-5.0 μL of plasmid was added and mixed well (where the total amount of DNA was about 1.0 μg), and allowed to stand in an ice bath for 5-10 min.

(3) The system was added into a pre-cooled 0.1 cm electroporation cuvette and received 2 electric shocks at 1.8 KV for 5 ms each.

(4) 1.0 mL of preheated recovery medium (LBWS) was quickly added, mixed well and transferred to a new 1.5 mL sterile centrifuge tube. The system was allowed to stand in a water bath at 46° C. for 6 min, and then stand in an ice bath.

(5) The cells were placed on a travelling shaker (100 rpm) and incubated at 30° C. for 2 h.

(6) The cells were centrifuged for 1 min at 6,000 rpm and normal temperature, coated onto a detection plate of corresponding resistant transformant, and incubated in an incubator at a constant temperature of 30° C. for 2-3 days.

(7) Efficiency verification of competent cells: 5.0 μL of sterile $ddH_2O$ was added as a negative control, no colonies were grown. For the positive control, 1-5 μL of the plasmid pXMJ19 (where the total DNA content was about 1.0 μg) was added, a large number of colonies were grown. The correctly sequenced colonies were the recombinant *Corynebacterium glutamicum*.

Example 3. Effect of Over-Expression of SugR Gene on N-Acetylglucosamine Production in Recombinant *Corynebacterium glutamicum*

The correctly sequenced recombinant *Corynebacterium glutamicum* strain containing the plasmid pJYW-4-ceN-C.glglmS-SugR was inoculated from a glycerol tube into an LBG plate (added with 25 mg/L kanamycin sulfate), and cultured at 220 rpm and 30° C. for 18 h. Then single colonies were picked up and inoculated into an LBG plate until a large number of colonies were grown.

A loop of single colonies was inoculated to the seed culture medium, and cultured at 220 rpm and 30° C. for 16 to 18 h until the cells were grown to the early logarithmic phase.

10% of the seed culture was inoculated into the fermentation medium and incubated at 30° C. and 220 rpm for 72 h. The amount of GlcNAc produced was determined.

Figure 1:
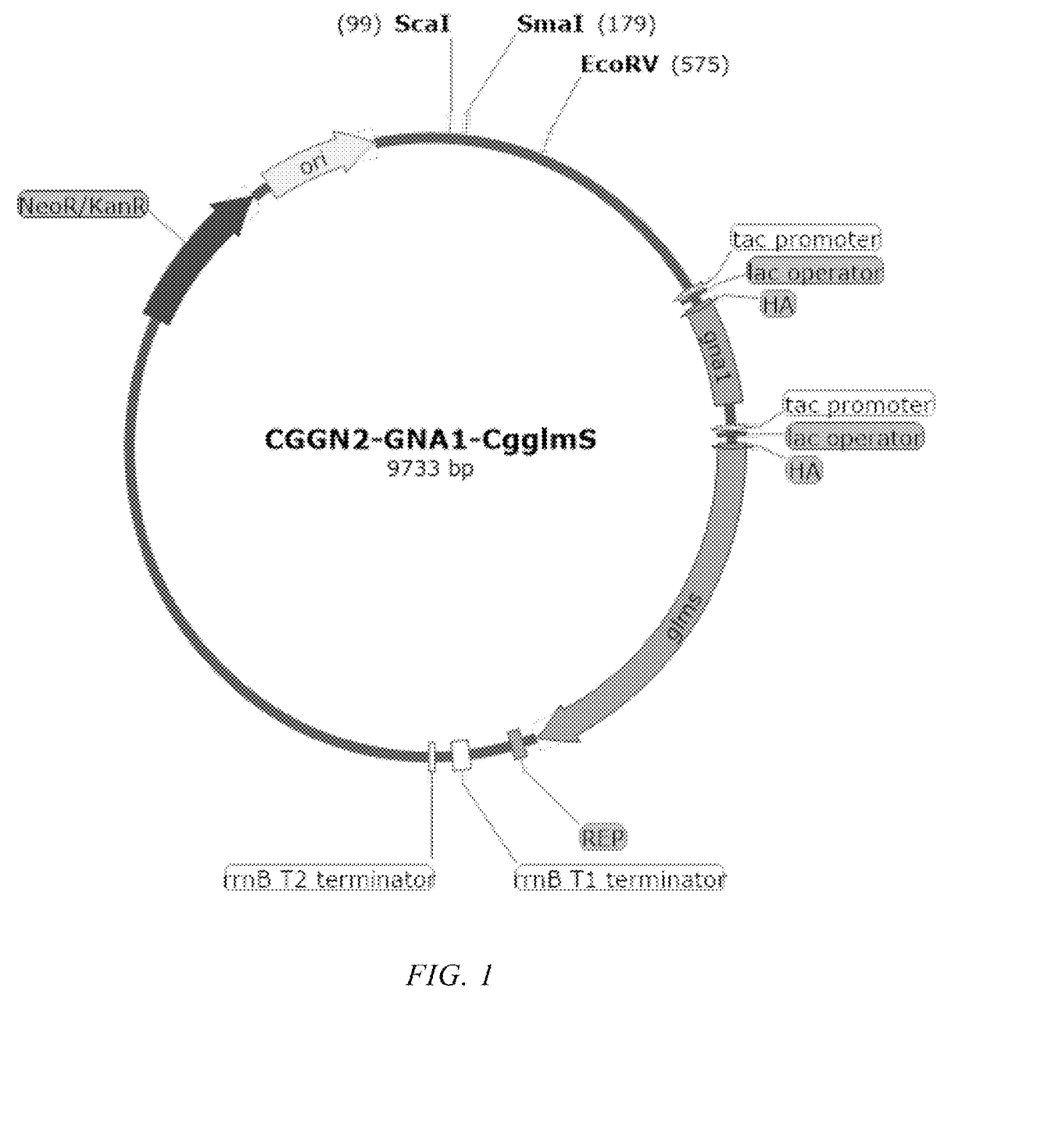
FIG. 1 shows the map of pJYW-4-ceN-C.glglmS plasmid.
Figure 2:
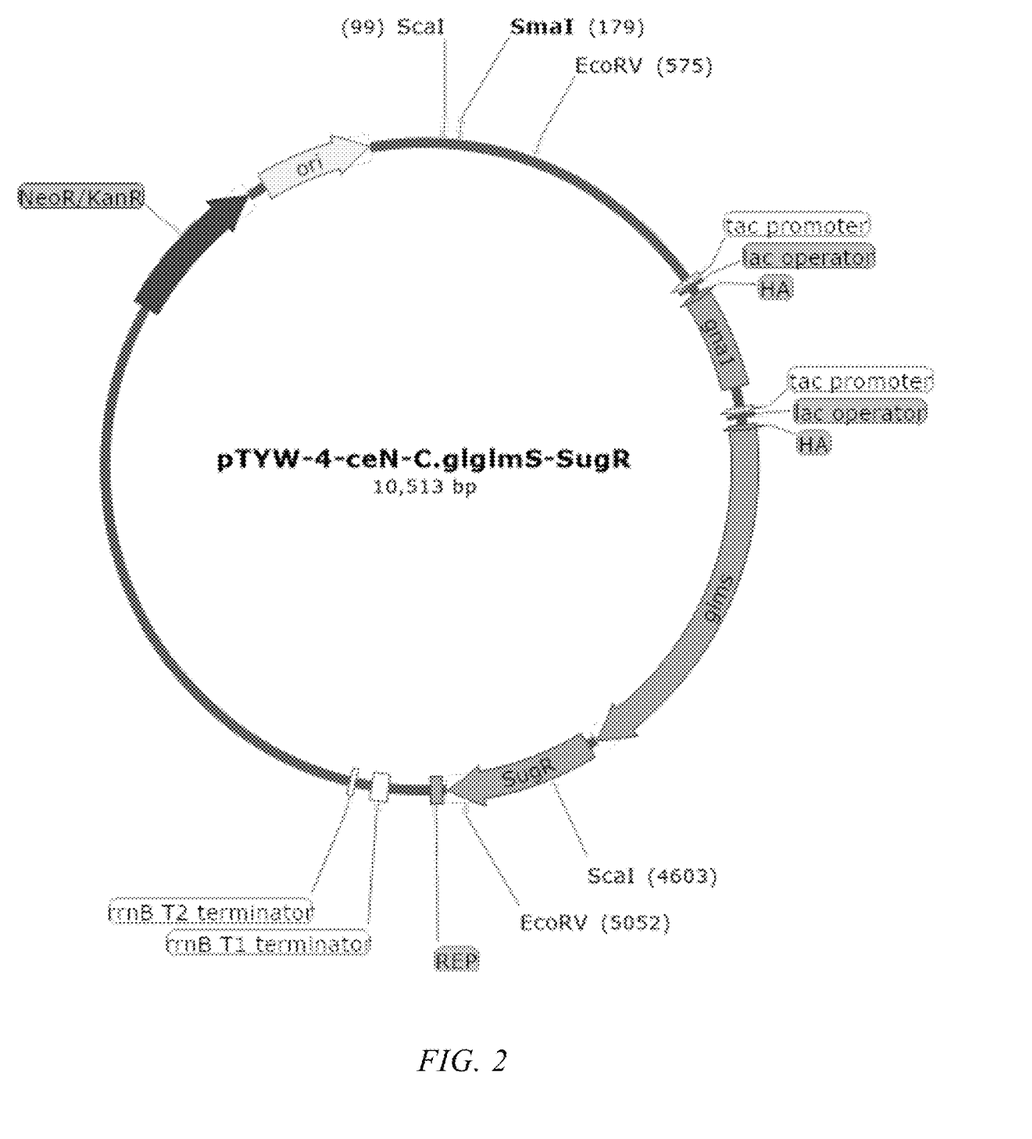
FIG. 2 shows the map of the constructed recombinant pJYW-4-ceN-C.glglmS-SugR plasmid.
Figure 3:
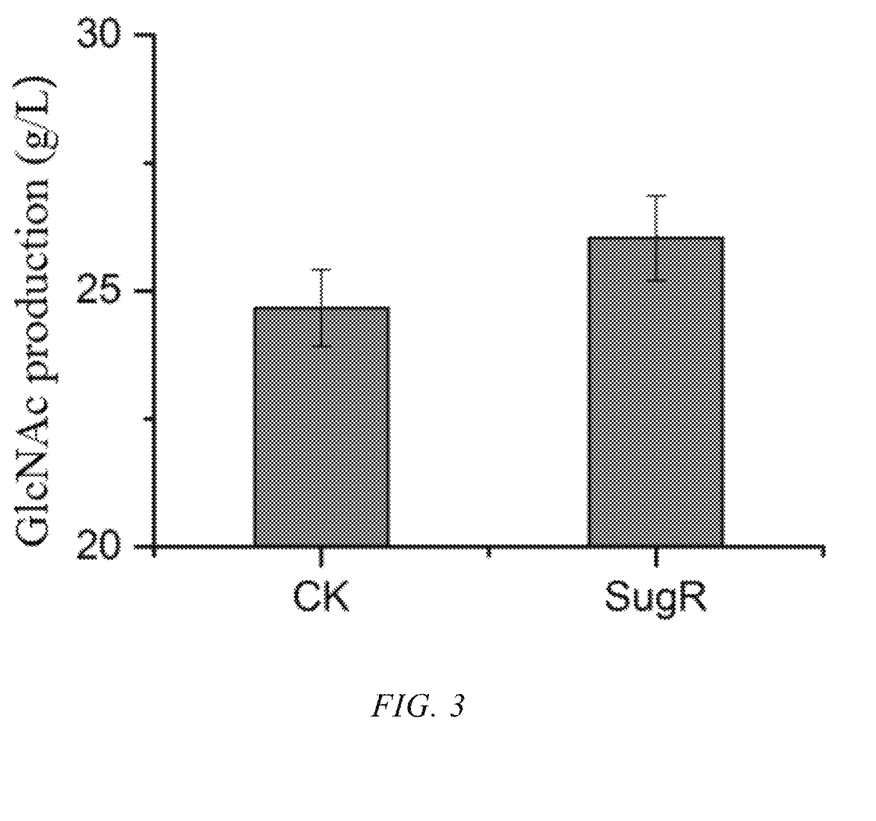
FIG. 3 shows the GlcNAc production in supernatants of shake flask fermentation with different strains.

The recombinant strain containing the plasmid pJYW-4-ceN-C.glglmS was used as a control, and cultured and fermented under the same conditions. After 72 h, the amount of GlcNAc is 24.7 g/L (CK as shown in FIG. 3), and the amount of GlcNAc produced by the SugR gene-over-expressing strain containing the plasmid pJYW-4-ceN-C.glglmS-SugR over 72 h was 26 g/L (SugR as shown in FIG. 3).

While preferred embodiments of the present invention have been described above, the present invention is not limited thereto. It should be appreciated that some improvements and variations can be made by those skilled in the art without departing from the technical principles of the present invention, which are also contemplated to be within the scope of the present invention.

What is claimed is:

1. A recombinant *Corynebacterium glutamicum* producing N-acetylglucosamine, wherein the recombinant *Corynebacterium glutamicum* expresses a transcription factor SugR, wherein said recombinant *Corynebacterium glutamicum* comprises the expression vector pJYW-4-ceN-C.glglmS-SugR, and wherein said transcription factor SugR is encoded by said expression vector.

2. The recombinant *Corynebacterium glutamicum* according to claim 1, wherein the acetylglucosamine deacetylase coding gene NagA, the acetylglucosamine deaminase coding gene GamA and the L-lactate dehydrogenase coding gene ldh in the *Corynebacterium glutamicum* are knocked out.

3. The recombinant *Corynebacterium glutamicum* according to claim 1, wherein the *Corynebacterium glutamicum* is *C. glutamicum* S9114 ΔnagA-ΔgamA-Δldh.

4. A method for constructing a recombinant *Corynebacterium glutamicum* according to claim 1, comprising a step of:

transforming a host bacterium with the expression vector pJYW-4-ceN-C.glglmS-SugR to obtain the recombinant *Corynebacterium glutamicum* producing N-acetylglucosamine, wherein the host bacterium is *Corynebacterium glutamicum* in which the acetylglucosamine deacetylase coding gene NagA, the acetylglucosamine deaminase coding gene GamA, and the L-lactate dehydrogenase coding gene ldh are knocked out.

5. The method according to claim 4, wherein the host bacterium is *C. glutamicum* S9114 ΔnagA-ΔgamA-Δldh, which is constructed by the steps of:

knocking out the acetylglucosamine deacetylase coding gene NagA, the acetylglucosamine deaminase coding gene GamA and the L-lactate dehydrogenase coding gene ldh in *C. glutamicum* S9114 sequentially by using a gene knockout frame of the acetylglucosamine deacetylase coding gene NagA, a gene knockout frame of the acetylglucosamine deaminase coding gene GamA, and a gene knockout frame of the L-lactate dehydrogenase coding gene ldh.

\* \* \* \* \*